United States Patent [19]

Ötvös et al.

[11] Patent Number: 5,767,264
[45] Date of Patent: Jun. 16, 1998

[54] OLIGODEOXYNUCLEOTIDES CONTAINING 5-ALKYL, 5-(1-ALKENYL)- AND 5-(1-ALKYNL) PYRIMIDINES

[75] Inventors: László Ötvös; János Sägi; Attila Szemző ; Gyula Sági; Ottóné Szabolcs; Éva Ruff; Katalin Ébinger; Ferencné Tüdős; Irén Fellegvári, all of Budapest, Hungary

[73] Assignee: MTA Zozponti Kemiai Kutato Intezet, Budapest, Hungary

[21] Appl. No.: 934,852

[22] Filed: Sep. 22, 1997

Related U.S. Application Data

[63] Continuation-in-part of Ser. No. 492,043, Sep. 21, 1995, abandoned.

[30] Foreign Application Priority Data

Jan. 21, 1994 [HU] Hungary ................. 93 000164

[51] Int. Cl.⁶ ........................ C07H 21/00; C07H 21/04
[52] U.S. Cl. ................ 536/24.5; 536/23.1; 536/24.1
[58] Field of Search ................... 514/44; 536/23.1, 536/24.5, 24.1; 935/33, 55

[56] References Cited

U.S. PATENT DOCUMENTS 5,484,908  1/1996  Froehler et al. ............. 536/24.31

OTHER PUBLICATIONS

Kim, S. "The Influence of oligodeoxyribonucleotide phosphorothioate pyrimidine strands on triplex formation." *FEBS* vol. 314 (1) pp. 29–32 Dec. 1992.

Xodo, et al "Effect of 5-metlylcytosine on the stability of triple stranded DNA –a thermodynamic study." *NAR* vol. 19(20) 1991 pp. 5625–5631.

Froeitzer et al "Oligodeoxynucleotides containing C-5 Propyne Analogs of 2'-Deoxyuridine and 2' Deoxycytidine." *Tetrahedron Letters*, vol. 33(37) pp. 5307–5310 1992.

*Primary Examiner*—George C. Elliott
*Assistant Examiner*—Sean M'Garry
*Attorney, Agent, or Firm*—Keil & Weinkauf

[57] ABSTRACT

A 12 to 30 nucleotide-unit long oligonucleotide that comprises at least one 5-substituted uracil or cytosine, where the 5-substituent is a $C_{3-6}$ n-alkyl, a vinyl, a butenyl, an ethynyl, or a $C_{4-12}$ n-1-alkynyl, with the proviso that the uracil moiety may not be substituted with an n-alkyl or a $C_{8-12}$ n-1-alkynyl.

3 Claims, 6 Drawing Sheets

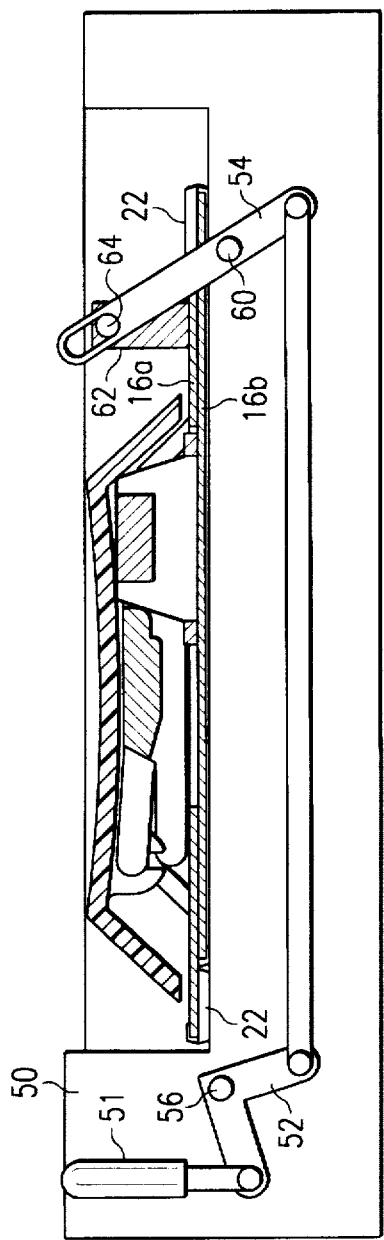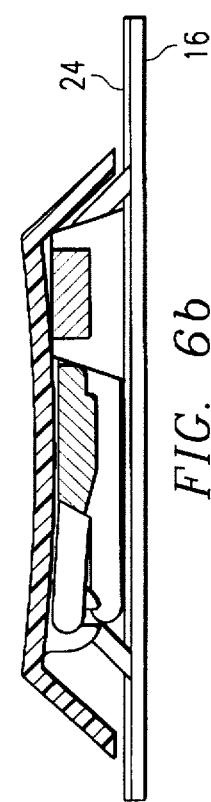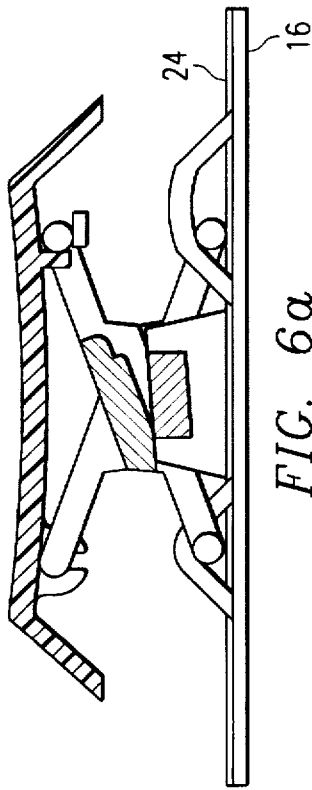

OLIGODEOXYNUCLEOTIDES CONTAINING 5-ALKYL, 5-(1-ALKENYL)- AND 5-(1-ALKYNL) PYRIMIDINES

This application is a continuation in part of 08/492,043, filed Sep. 21, 1995 and now abandoned.

The invention relates to oligodeoxynucleotides containing 5-alkyl-, 5-(1-alkenyl)- and 5-(1-alkynyl) pyrimidines and to pharmaceutical compositions containing such compounds. Furthermore, the invention relates to a process for the preparation of such compounds and compositions.

More specifically, the invention relates to therapeutically usable 12 to 30 nucleotide-unit long oligodeoxynucleotides that contain at least one 5-substituted pyrimidine base, either uracil or cytosine, where the 5-substituent is a $C_{3-14}$ n-alkyl group, a $C_{2-8}$ (E)-n-1-alkenyl group, an ethynyl or a $C_{4-12}$ n-1-alkynyl group.

It is known that oligonucleotides can regulate gene expression by sequence-specific binding to a double-stranded DNA through formation of a triple helix or to a single-stranded RNA through formation of a double helix. Binding to a specific region of a double-stranded DNA involved in the biosynthesis of exogenous pathogens like viruses, fungi or bacteria or an endogenous one like an oncogene, transcription of the specific region of DNA is inhibited by the formation of triple helix. This is called anti-gene effect.

Inhibition of gene expression by oligonucleotides through formation of double helix with a specific region of an RNA, messenger RNA (mRNA) or virus RNA, is called antisense inhibition. The oligonucleotides exerting their effect in this way are called antisense oligonucleotides. Antisense inhibition of expression of mRNA means inhibition of translation, i.e. the protein synthesis. Antisense inhibition of expression of viral RNA means inhibition of RNA replication or reverse transcription like in the case of HIV. While the conventional drugs bind to the target molecule, usually a biopolymer like an enzyme, with 2–3 bonds, the antisense oligonucleotides bind to the target RNA at as many sites with 2–3 hydrogen bonds as many monomeric units, called nucleotides, the antisense oligonucleotides contain. This is the basis of the exceptionally high specificity of the antisense oligonucleotides. For therapeutical use the antisense oligonucleotides should have the following properties:

i) ability to cross efficiently cell membrane to reach appropriate concentration within the target cell, referred to hereinafter as cellular uptake;

ii) high stability against degradation by nucleases both in the serum and cells, referred to hereinafter as nuclease-stability, and iii) ability to form stable double helix with the defined region of the target RNA within the cell in a sequence-specific manner, referred to hereinafter as duplex stability.

According to literature data these properties can not be accomplished with antisense oligonucleotides composed of natural nucleotides. Therefore, it was necessary to elaborate chemical modification of the oligonucleotides to meet the above requirements. Chemical modification can be performed in each of the three components of the nucleotide unit of the oligonucleotide (Scheme 1):

i) heterocyclic base, ii) sugar moiety, or iii) the phosphodiester linkage.

Numerous modifications of the phosphodiester linkage have been described (Scheme 1):

Scheme 1

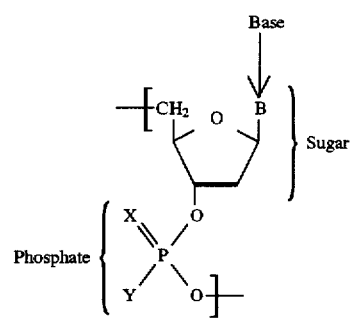

1. X=O; Y=S
2. X=Y=S
3. X=O; Y=NH-R
4. X=O; Y=alkyl group.

Among these modifications the one under 1 is most widespread. All of the above modifications increase nuclease-stability but in most cases they decrease duplex stability of the oligodeoxynucleotide. Except for compound 2, the substitution of the non-bridging oxygen results in chiral phosphorus atom. Number of theoretically possible diastereomers is $2^n$, where n is the number of nucleotides in the oligonucleotide (E. Uhlman & A. Peyman: Chem. Rev. 1990, 90, 543–583).

A comprehensive collection of the chemical modifications published so far can be found in Antisense Research and Development 1991, 1, 66–112; ibid. 1992, 2, 64–107; and E. Uhlman & A. Peyman: Chem. Rev. 1990, 90, 543–583. Based on these literature references only a few chemical modifications of pyrimidine bases have been described from which 5-bromo and 5-methyl substitutions of the cytosine increase duplex stability but do not increase nuclease-stability (P. Dan Cook, Anti-Cancer Drug Design 1991, 6, 585–607; O. Kemal et al., Nucleosides & Nucleotides 1991, 10, 555–561). Replacement of 5-methyl group of thymine by a (4-aminobutylamino)methyl group and 6-aza substitution of thymine increase nuclease-stability but decrease duplex stability (T. Takeda et al., Chem. Pharm. Bull. 1987, 35, 3558–3567; Y. S. Sanghvi et al. Nucleosides & Nucleotides 1991, 10, 345–6).

According to a recent publication if 5-(1-propynyl)-uracil or 5-(1-propynyl)cytosine is incorporated in place of thymine or cytosine, respectively, into an oligodeoxynucleotide, the duplex stability with a complementary RNA oligomer increases (B. C. Froehler et al., Tetrahedron Letters 1992, 33, 5307–5310). Although this modification increases nuclease-stability to a small extent as well, the increase is by orders of magnitude less than that observed with phosphorothioate-modified oligodeoxynucleotides (modification 1, above). The 5-(1-propynyl) substitution of pyrimidines hardly increases oligodeoxynucleotide hydrophobicity which is in close correlation with cellular uptake.

It is the object of the present invention to synthetize oligodeoxynucleotides with unaltered or increased duplex stability and highly increased nuclease-stability as well as strongly increased hydrophobicity and cellular uptake properties.

The invention is based on the recognition that if at least one nucleotide unit of a 12–30 nucleotide-unit long oligodeoxynucleotide contains a 5-substituted pyrimidine base where the 5-substituent is a $C_{3-14}$ n-alkyl group, a $C_{2-8}$ (E)-n-1-alkenyl group, an ethynyl or a $C_{4-12}$ n-1-alkynyl group, the oligodeoxynucleotide possesses unaltered or increased duplex stability, highly increased nuclease-stability as well as strongly increased hydrophobicity and cellular-uptake properties.

Based on the above, the invention relates to oligodeoxynucleotides composed of 12 to 30 monomeric units that contain at least one 5-substituted pyrimidine base, either uracil or cytosine, where the 5-substituent is a $C_{3-14}$ n-alkyl group, a $C_{2-8}$ (E)-n-1-alkenyl group, an ethynyl or a $C_{4-12}$ n-1-alkynyl group, with the proviso that the uracil moiety may not be substituted with an n-alkyl group or a $C_{8-12}$ n-1alkynyl group.

In an advantageous group of the compounds according to the invention one or more of the phosphodiester moieties are replaced by phosphorothioate or phosphorodithioate moieties.

In a further advantageous group of the compounds according to the invention one or more of the phosphodiester moieties are replaced by phosphorothioate moieties of R- or S-configuration.

The group of compounds according to the invention also possesses advantageous properties in which the pyrimidine base is a 5-substituted uracil where the 5-substituent is a $C_{3-14}$ n-alkyl group, a $C_{2-4}$ (E)-n-1-alkenyl group or a $C_{5-8}$ n-1-alkynyl group.

Another advantageous group of componds according to the invention contains a 5-substituted cytosine as pyrimidine base where the 5-substituent is a $C_{3-14}$ n-alkyl group, a $C_{2-4}$ (E)-n-1-alkenyl group, or a $C_{5-8}$ n-1-alkynyl group.

BRIEF DESCRIPTION OF THE DRAWINGS

FIG. 1 depicts a linear increase to (octyl$^5$U-dA)$_{10}$ and (octynyl$^5$dU-dA)$_{10}$. FIG. 2 depicts a linear increase to (octyl$^5$dC-dG)$_6$ and (octynyl$^5$dC-dG)$_6$.

FIG. 3 shows that cellular uptake of oligonucleotides increased upon substitution of position 5 of uracil by 1-alkynyl groups.

Figure 1:
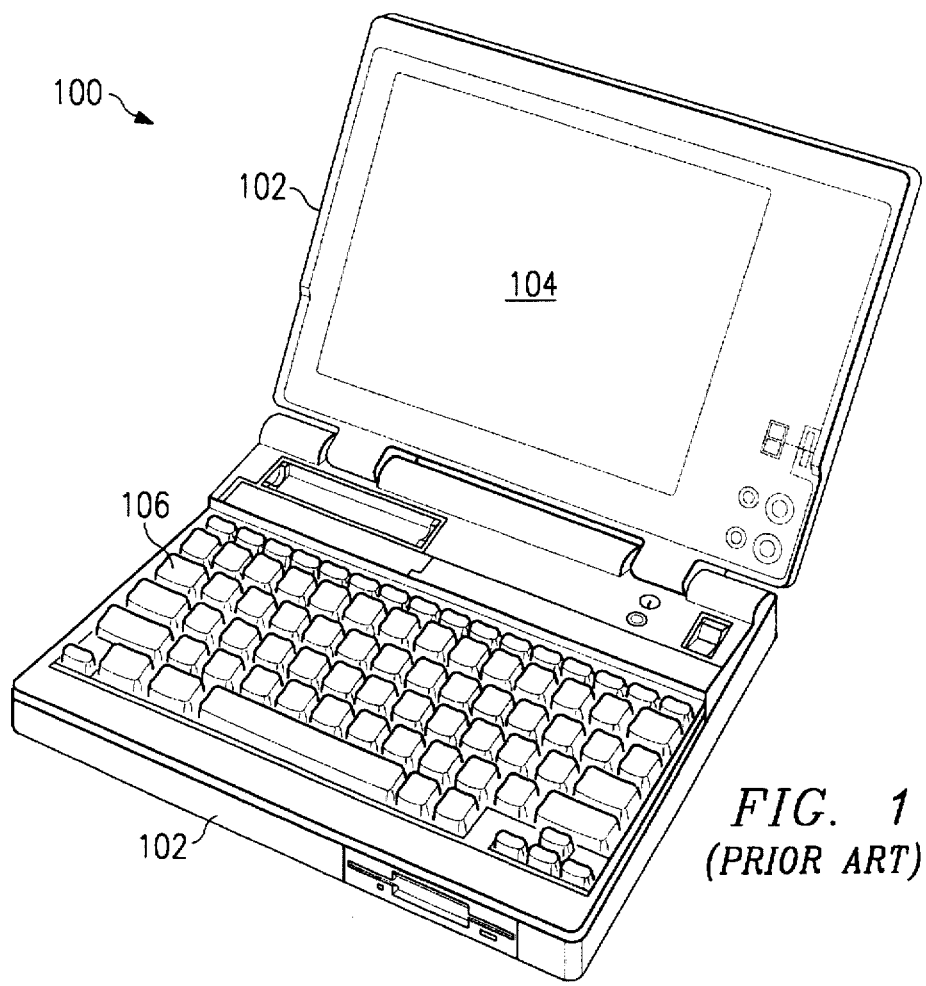
FIGS. 1 and 2 depict a correlation between carbon chain length of the hydrophobic substituent and hydrophobicity of the oligonucleotide [log(k')], calculated from HPLC retention times, where the increase is linear up to the 8-carbon atom chain containing analogs.

The advantageous properties of the compounds according to the invention were proved by the following experiments.

Duplex stability

An antisense oligodeoxynucleotide, an oligomeric DNA, should be able to form a stable double helix or duplex with a defined region of the target RNA within the cell. This is called a DNA-RNA hybrid duplex. A DNA-RNA hybrid duplex is generally more stable than a DNA-DNA duplex. We have chosen deoxyoligonucleotides of self-complementary sequence, that is DNA-DNA duplexes, as model oligonucleotides for duplex stability experiments.

The structural stability of a nucleic acid duplex depends among others on the temperature. Stability of a duplex is therefore most often characterized by the stability of the duplex against heat-induced denaturation or thermal denaturation. Ultraviolet optical density of a nucleic acid solution depends on the secondary structure of a nucleic acid, that is on the fact whether the nucleic acid is a duplex or a denatured random coil. In this way, duplex stability can be characterized by parameters obtained from plots of ultraviolet optical density versus temperature or from melting profiles of nucleic acid solutions.

The results of our duplex stability experiments are given in Tables 1 to 7.

The most important data that can be obtained from the melting profiles is the midpoint of the thermal transition curve, called $T_m$ (°C.). $T_m$ is the temperature where 50% of the duplex becomes a random coil, that is denatured. The $T_m$ is reproducible within 0.1° C. with polydeoxynucleotides or DNA and within 1° C. with oligodeoxynucleotides. The second data given in the Tables is the heat-induced increase of molar exctinction coefficient or thermal hyperchromicity at a given wavelength ($H_{260}$ or $H_{280}$). This provides a measure of denaturability and thus refers to the helix content of the undenatured duplex. More specifically, the H-value is the increase of optical density, in percent, of the nucleic acid solution at a given wavelength. The third parameter is dT, the temperature range between 25 to 75% of the H-value. The dT value characterizes cooperativity of the thermal transition which refers to the mechanism of transition. With natural polydeoxynucleotide duplexes dT is less than 1° C. With oligodeoxynucleotide duplexes dT is higher than 5° C.

Duplex stability of a nucleic acid depends also on the ionic strength of the solution. Duplex stability experiments with compounds according to the invention were carried out in a buffer of ionic strength close to physiological serum conditions. In special cases buffers differing from these ionic conditions in both directions were also applied:

1. Physiological buffer: 0.1M NaCl, 20 mM sodium phosphate (pH 7.2), 2 mM $MgCl_2$;
2. High-salt buffer for measuring duplex stability of the low-stability adenine-thymine and analogs-containing oligodeoxynucleotides: 0.5M NaCl, 20 mM Tris.HCl (pH 7.5), 10 mM $MgCl_2$;
3. Low-salt buffer for measuring duplex stability of the highly stable guanine-cytosine and analogs-containing oligodeoxynucleotides: 10 mM buffered $Na^+$, pH 7.6.

Thermal melting profiles were determined in a Hewlett-Packard HP8452A diode-array spectrophotometer interfaced to an IBM-compatible AT 386 computer through an AD-card. The cell holder was heated by transistors. The software "Absorbe" written for this purpose (CheMicro Ltd., Budapest) regulated linear heating of the oligodeoxynucleotide solution, generally with a rate of 0.5° C./min, in a 1 cm path-length cell of 0.7 ml volume, collected absorption and temperature data measured within the cell with a platinum probe, and performed calculation of parameters characterizing thermal transitions. $T_m$ was calculated from the 1st derivative of the smoothed absorption versus temperature profile. oligodeoxynucleotide concentrations were 1.0+/−0.1 optical density units (at 260 nm)/ml. Data given in the Tables are mean values of at least two measurements.

TABLE 1

Duplex stability of 5'-(n-alkyl$^5$dU-dA)$_{10}$-3' oligodeoxynucleotides according to the invention

| Oligodeoxy-nucleotide | High-salt buffer | | | Physiological | | |
|---|---|---|---|---|---|---|
| | $T_m$ (°C.) | $H_{260}$ (%) | dT (°C.) | $T_m$ (°C.) | $H_{260}$ (%) | dT (°C.) |
| (Propyl$^5$dU-dA)$_{10}$ | 40.7 | 25.0 | 15.2 | 34.9 | 25.2 | 12.7 |
| (Butyl$^5$dU-dA)$_{10}$ | 39.1 | 24.3 | 16.6 | 33.8 | 24.6 | 14.3 |

TABLE 1-continued

Duplex stability of 5'-(n-alkyl$^5$dU-dA)$_{10}$-3'
oligodeoxynucleotides according to the invention

| Oligodeoxy-nucleotide | High-salt buffer | | | Physiological buffer | | |
|---|---|---|---|---|---|---|
| | T$_m$ (°C.) | H$_{260}$ (%) | dT (°C.) | T$_m$ (°C.) | H$_{260}$ (%) | dT (°C.) |
| (Pentyl$^5$dU-dA)$_{10}$ | 38.8 | 13.8 | 14.5 | 32.1 | 18.7 | 15.0 |
| (Hexyl$^5$dU-dA)$_{10}$ | 7.8 | 14.0 | 8.2 | — | | |
| (Octyl$^5$dU-dA)$_{10}$ | <5 | | — | | | |
| (Tetradecyl$^5$dU-dA)$_{10}$ | <5 | | — | | | |
| (dT-dA)$_{10}$ | 53.4 | 30.3 | 16.7 | 47.4 | 27.5 | 12.9 |

The formula 5'-(n-alkyl$^5$dU-dA)$_{10}$-3' refers to 20 nucleotide-unit long oligodeoxynucleotides composed of 5-n-alkyl-dUMP$^{3O}$ and dAMP$^{++}$ nucleotides connected by phosphodiester linkages and the sequence is strictly alternating. The termini are 5-n-alkyl-2'-deoxyuridine with a free 5'-OH group (5'-end of the oligodeoxynucleotide) and 2'-deoxyadenosine with a free 3'-OH group (3'-end of the oligodeoxynucleotide).

$^+$ dUMP=2'-deoxyuridine-5'-triphosphate
$^{++}$ dAMP=2'-deoxyadenosine-5'-triphosphate

TABLE 2

Duplex stability of 5'-(1-n-alkenyl$^5$dU-dA)$_{10}$-3'
oligodeoxynucleotides according to the invention

| Oligodeoxy-nucleotide | Physiological buffer | | |
|---|---|---|---|
| | T$_m$ (°C.) | H$_{260}$ (%) | dT (°C.) |
| (Vinyl$^5$dU-dA)$_{10}$ | 44.1 | 12.3 | 17.5 |
| (Butenyl$^5$dU-dA)$_{10}$ | 46.2 | 12.3 | 17.7 |
| (dT-dA)$_{10}$ | 47.4 | 27.5 | 12.9 |

The formula 5'-(1-n-alkenyl$^5$dU-dA)$_{10}$-3' refers to 20 nucleotide-unit long oligodeoxynucleotides composed of (E)-5-(1-n-alkenyl)-dUMP and dAMP nucleotides connected by phosphodiester linkages and the sequence is strictly alternating. The termini are (E)-5-(1-n-alkenyl)-2'-deoxyuridine with a free 5'-OH group and 2'-deoxyadenosine with a free 3'-OH group.

TABLE 3

Duplex stability of 5'-(1-n-alkynyl$^5$dU-dA)$_{10}$-3'
oligodeoxynucleotides according to the invention

| Oligodeoxy-nucleotide | Physiological buffer | | |
|---|---|---|---|
| | T$_m$ (°C.) | H$_{260}$ (%) | dT (°C.) |
| (Pentynyl$^5$dU-dA)$_{10}$ | 54.4 | 25.3 | 12.6 |
| (Hexynyl$^5$dU-dA)$_{10}$ | 52.0 | 23.4 | 16.6 |
| (Heptynyl$^5$dU-dA)$_{10}$ | 43.7 | 22.5 | 15.6 |
| (Octynyl$^5$dU-dA)$_{10}$ | 18.3 | 15.6 | 7.9 |
| (dT-dA)$_{10}$ | 47.4 | 27.5 | 12.9 |

The formula 5'-(1-n-alkynyl$^5$dU-dA)$_{10}$-3' refers to 20 nucleotide-unit long oligodeoxynucleotides composed of 5-(1-n-alkynyl)-dUMP and dAMP nucleotides connected by phosphodiester linkages and the sequence is strictly alternating. The termini are 5-(1-n-alkynyl)-2'-deoxyuridine with a free 5'-OH group and 2'-deoxyadenosine with a free 3'-OH group.

TABLE 4

Duplex stability of 5'-(n-alkyl$^5$dC-dG)$_6$-3'
oligodeoxynucleotides according to the invention

| Oligodeoxy-nucleotide | Low-salt buffer | | | Physiological buffer | | |
|---|---|---|---|---|---|---|
| | T$_m$ (°C.) | H$_{260}$ (%) | dT (°C.) | T$_m$ (°C.) | H$_{260}$ (%) | dT (°C.) |
| (Butyl$^5$dC-dG)$_6$ | 80.6 | 19.2 | 21.8 | — | | |
| (Pentyl$^5$dC-dG)$_6$ | 79.3 | 26.1 | 20.1 | — | | |
| (Hexyl$^5$dC-dG)$_6$ | 75.8 | 25.5 | 23.4 | 75.4 | 28.7 | 27.9 |
| (Octyl$^5$dC-dG)$_6$ | 42.4 | 19.9 | 24.9 | 27.2 | 22.2 | 21.1 |
| (dC-dG)$_6$ | 79.7 | 38.0 | 16.5 | 82.9 | 55.7 | 14.3 |

The formula 5'-(n-alkyl$^5$dC-dG)$_6$-3' refers to 12 nucleotide-unit long oligodeoxynucleotides composed of 5-n-alkyl-dCMP$^+$ and dGMP$^{++}$ nucleotides connected by phosphodiester linkages and the sequence is strictly alternating. The termini are 5-n-alkyl-2'-deoxycytidine with a free 5'-OH group and 2'-deoxyguanosine with a free 3'-OH group.

$^+$ dCMP=2'-deoxycytidine-5'-triphosphate
$^{++}$ dGMP=2'-deoxyguanosine-5'-triphosphate

TABLE 5

Duplex stability of 5'-(n-1-alkynyl$^5$dC-dG)$_6$-3'
oligodeoxynucleotides according to the invention

| Oligodeoxy-nucleotide | Low-salt buffer | | | Physiological buffer | | |
|---|---|---|---|---|---|---|
| | T$_m$ (°C.) | H$_{260}$ (%) | dT (°C.) | T$_m$ (°C.) | H$_{260}$ (%) | dT (°C.) |
| (Ethynyl$^5$dC-dG)$_6$ | 95.2 | 14.9 | 16.4 | — | | |
| (Pentynyl$^5$dC-dG)$_6$ | 95.6 | 11.7 | 10.6 | >98 | | |
| (Hexynyl$^5$dC-dG)$_6$ | 95.9 | 13.5 | 12.6 | >98 | | |
| (Octynyl$^5$dC-dG)$_6$ | 90.0 | 18.1 | 16.0 | >90 | | |
| (dC-dG)$_6$ | 79.7 | 38.0 | 16.5 | 82.9 | 55.7 | 14.3 |

The formula 5'-(1-n-alkynyl$^5$dC-dG)$_6$-3' refers to 12 nucleotide-unit long oligodeoxynucleotides composed of 5-(1-n-alkynyl)-dCMP and dGMP nucleotides connected by phosphodiester linkages and the sequence is strictly alternating. The termini are 5-(1-n-alkynyl)-2'-deoxycytidine with a free 5'-OH group and 2'-deoxyguanosine with a free 3'-OH group.

TABLE 6

Duplex stability of 5'-(1-n-hexynyl$^5$dU-dA)$_{10}$-3'
oligodeoxynucleotides containing phosphorothioate linkages
according to the invention

| Oligodeoxy-nucleotide | Physiological buffer T$_m$ (°C.) |
|---|---|
| 1. 1,2-Thio-(hexynyl$^5$dU-dA)$_{10}$ | 51.2 |
| 2. 1,2,18,19-Thio-(hexynyl$^5$dU-dA)$_{10}$ | 50.5 |
| 3. Perthio-(hexynyl$^5$dU-dA)$_{10}$ | 44.0 |
| 4. 1,2-Dithio-(hexynyl$^5$dU-dA)$_{10}$ | 50.8 |
| (Hexynyl$^5$dU-dA)$_{10}$ | 52.0 |
| (dT-dA)$_{10}$ | 47.4 |
| Perthio-(dT-dA)$_{10}$ | 38.6 |

The formula 5'-(1-n-hexynyl$^5$dU-dA)$_{10}$-3' refers to a 20 nucleotide-unit long oligodeoxynucleotide composed of 5-(1-n-hexynyl)-dUMP and dAMP nucleotides connected by phosphodiester linkages and the sequence is strictly alternating. The termini are 5-(1-n-hexynyl)-2'-deoxyuridine with a free 5'-OH group and 2'-deoxyadenosine with a free 3'-OH group. Compound 1 contains a phosphorothioate linkage next to the 3'-terminus instead of the phosphodiester linkage. Compound 2 contains two phosphorothioate linkages next to both termini. In compound 3 each of the 19 phosphodiester linkages is replaced by a phoshorothioate linkage. Compound 4 contains a phoshorodithioate linkage next to the 3'-terminus.

TABLE 7

Duplex stability of 12-mer block oligodeoxynucleotides according to the invention

| 5'-3' Oligodeoxy-nucleotide | High-salt $T_m$ (°C.) | Physiological buffer $T_m$ (°C.) | Low-salt $T_m$ (°C.) |
|---|---|---|---|
| 1. $(dT)_6(dA)_6$ | 33.3 | — | — |
| 2. $(Hexynyl^5dU)_6(dA)_6$ | 53.5 | — | — |
| 3. $(dC)_6(dG)_6$ | — | — | 74.2 |
| 4. $(Hexynyl^5dC)_6(dG)_6$ | — | — | 95.7 |
| $(dT-dA)_{10}$ | 53.4 | 47.4 | — |
| $(dT-dA)_6$ | 40.2 | — | — |
| $(Hexynyl^5dU-dA)_{10}$ | 54.9 | 52.0 | — |
| $(dC-dG)_6$ | — | 82.9 | 79.7 |
| $(Hexynyl^5dC-dG)_6$ | — | >98 | 95.9 |

The block sequence means that the oligodeoxynucleotide is composed of blocks of homologous sequences. Compound 1 is a 12-mer oligodeoxynucleotide composed of six subsequent dTMP and six subsequent dAMP units connected by phosphodiester linkages and the termini are thymidine with a free 5'-OH group and 2'-deoxyadenosine with a free 3'-OH group. Compound 2 contains 5-(1-n-hexynyl)-dUMP units instead of thymidines. Compound 4 contains 5-(1-n-hexynyl)-dCMP units instead of 2'-deoxycytidine units.

The $T_m$ data in Tables 1–7 above prove that duplex stability of the oligodeoxynucleotides containing 5-n -alkyl-, 5-(n-1-alkenyl)- or 5-(n-1-alkynyl)pyrimidines in place of the unmodified pyrimidines is retained or increased, as compared to the duplex stability of the oligodeoxynucleotide of the same length and with unmodified pyrimidines. There is an exception when the pyrimidine base thymine is replaced by 5-n-alkyluracils (Table 1). However, if the pyrimidine base cytosine is replaced by 5-n-alkylcytosine, duplex stability is increased up to the 5-n-pentylcytosine (Table 4). If the pyrimidine base thymine is replaced by 5-(1-n-alkenyl)-uracil, duplex stability is retained (Table 2). If the pyrimidine base thymine is replaced by 5-(1-n-alkynyl)-uracils, duplex stability is increased up to the 5-(1-n -hexynyl) derivative (Table 3). If the pyrimidine base cytosine is replaced by 5-(1-n-alkynyl)cytosine, duplex stability is increased up to the 5-(1-n-octynyl) or even longer-chain derivatives (Table 5). Phosphorothioate substitution of the phosphodiester linkage is known to decrease duplex stability. Replacement of the pyrimidine base thymine by 5-(1-n-hexynyl)uracil increases duplex stability of the phosphorothioate-substituted oligodeoxynucleotides as well (Table 6). The increase in the duplex stability upon replacement of the pyrimidine base thymine or cytosine by 5-(1-n-alkynyl)uracil or 5-(1-n-alkynyl)cytosine is even higher if the sequence of the oligodeoxynucleotide is not alternating but if the modified pyrimidines are side by side (Table 7).

Cellular uptake
Hydrophobicity of the oligodeoxynucleotide analogs

It is known from the literature that hydrophobicity of a polyanionic oligodeoxynucleotide correlates well with its cellular uptake. Cellular uptake of the oligodeoxynucleotides can best be studied with their labelled form, either radioactive or non-radioactive. In this way, a comparative determination of hydrophobicity of novel oligodeoxynucleotide analogs provides information for their comparative cellular uptake.

High-performance liquid chromatography (HPLC) can be used for determination of hydrophobicity. For example, HPLC retention times were recently used for the determination of hydrophobicity of nucleoside derivatives (Valkó et al., *J. Liq. Chromatogr.* 1989, 12, 2103–2116). We extended this method also to oligodeoxynucleotides.

HPLC examinations were carried out by using an ISCO instrument with model 2350 pumps and V4 ultraviolet detector. The pumps were programmed by an IBM compatible AT286 interfaced to the ISCO with the software ISCO ChemSearch version 2.3. In addition to programming the pumps, the software performed data aquisition and calculations. Retention time $(t_R)$ of oligodeoxynucleotides on a reverse-phase C18 column (Nucleosil 5 micrometer, 300 Å, 250×4.6 mm, Phenomenex, Torrence, Calif., USA) was determined with an acetonitrile gradient (5 to 50% in 45 minutes, 0.1M sodium phosphate buffer, pH 7). Flow rate was 1 ml/min and peaks were detected at 260 or 280 nm. The column-independent retention of a compound on a matrix (k') can be determined by the formula $(t_R-t_0)/t_0$, where $t_R$ is retention time of the compound and $t_0$ was 2.5 and 2.73 minutes, respectively, on the C18 column used. The parameter used for characterizing hydrophobicity is log(k'). Our experimental results are given in Tables 8 and 9.

TABLE 8

Hydrophobicity of 5'-(dT-dA)$_{10}$-3' analogs based on retention on a reversed-phase HPLC column ($t_0$ = 2.5 min)

| Oligodeoxynucleotide | $t_R$ (minutes) | k' | log(k') |
|---|---|---|---|
| $(Propyl^5dU-dA)_{10}$ | 22.2 | 7.88 | 0.8965 |
| $(Butyl^5dU-dA)_{10}$ | 26.2 | 9.48 | 0.9768 |
| $(Pentyl^5dU-dA)_{10}$ | 30.7 | 11.28 | 1.0523 |
| $(Hexyl^5dU-dA)_{10}$ | 35.2 | 13.08 | 1.1166 |
| $(Octyl^5dU-dA)_{10}$ | 47.2 | 17.88 | 1.2524 |
| $(Tetradecyl^5dU-dA)_{10}$ | 55.0 | 21.0 | 1.3222 |
| $(Vinyl^5dU-dA)_{10}$ | 20.1 | 7.04 | 0.8476 |
| $(Butenyl^5dU-dA)_{10}$ | 25.3 | 9.12 | 0.960 |
| $(Pentynyl^5dU-dA)_{10}$ | 24.8 | 8.92 | 0.9504 |
| $(Hexynyl^5dU-dA)_{10}$ | 31.0 | 11.4 | 1.0569 |
| $(Heptynyl^5dU-dA)_{10}$ | 36.6 | 13.64 | 1.1348 |
| $(Octynyl^5dU-dA)_{10}$ | 42.0 | 15.8 | 1.1987 |
| $(dT-dA)_{10}$ | 17.0 | 5.80 | 0.7634 |
| $(Propynyl^5dU-dA)_{10}$ | 18.0 | 6.2 | 0.7924 |

The formula 5'-(dT-dA)$_{10}$-3' refers to a 20 nucleotide-unit long oligodeoxynucleotide composed of dTTP and dAMP nucleotides connected by phosphodiester linkages and the sequence is strictly alternating. The termini are thymidine with a free 5'-OH group and 2'-deoxyadenosine with a free 3'-OH group. The compounds listed under the heading "Oligodeoxynucleotide" are analogs of (dT-dA)$_{10}$ where the thymidine dT nucleoside is replaced by 5-n-alkyl-, 5-(1-n-alkenyl)- and 5-(1-n-alkynyl)-2'-deoxyuridine nucleoside units. The parameters $t_R$, $t_0$, k' and log(k') are defined above.

TABLE 9

Hydrophobicity of 5'-(dC-dG)$_6$-3' analogs based on retention on a reversed-phase HPLC column ($t_0$ = 2.73 min)

| Oligodeoxynucleotide | $t_R$ (minutes) | k' | log(k') |
|---|---|---|---|
| $(Butyl^5dC-dG)_6$ | 16.5 | 5.04 | 0.7024 |
| $(Pentyl^5dC-dG)_6$ | 20.0 | 6.33 | 0.8014 |

TABLE 9-continued

Hydrophobicity of 5'-(dC-dG)₆-3' analogs based on
retention on a reversed-phase HPLC column (t₀ = 2.73 min)

| Oligodeoxynucleotide | $t_R$ (minutes) | k' | log(k') |
|---|---|---|---|
| (Hexyl⁵dC-dG)₆ | 25.7 | 8.41 | 0.9248 |
| (Octyl⁵dC-dG)₆ | 39.3 | 13.40 | 1.1271 |
| (Ethynyl⁵dC-dG)₆ | 16.6 | 5.08 | 0.7059 |
| (Pentynyl⁵dC-dG)₆ | 24.4 | 7.94 | 0.8998 |
| (Hexynyl⁵dC-dG)₆ | 28.8 | 9.55 | 0.9800 |
| (Octynyl⁵dC-dG)₆ | 40.8 | 13.94 | 1.1443 |
| (dC-dG)₆ | 11.0 | 3.03 | 0.4814 |
| (Methyl⁵dC-dG)₆ | 11.8 | 3.32 | 0.5211 |
| (Ethyl⁵dC-dG)₆ | 13.6 | 3.98 | 0.5999 |

The formula 5'-(dC-dG)₆-3 ' refers to a 12 nucleotide-unit long oligodeoxynucleotide composed of dCMP and dGMP nucleotides connected by phosphodiester linkages and the sequence is strictly alternating. The termini are 2'-deoxycytidine with a free 5'-OH group and 2'deoxyguanosine with a free 3'-OH group. The compounds listed under the heading "Oligodeoxynucleotide" are analogs of (dC-dG)₆ where the 2'-deoxycytidine dC nucleoside is replaced by 5-n-alkyl- and 5-(1-n-alkynyl) -2'-deoxycytidine nucleoside units. The parameters $t_R$, $t_0$, k' and log(k') are defined above.

Figure 2:
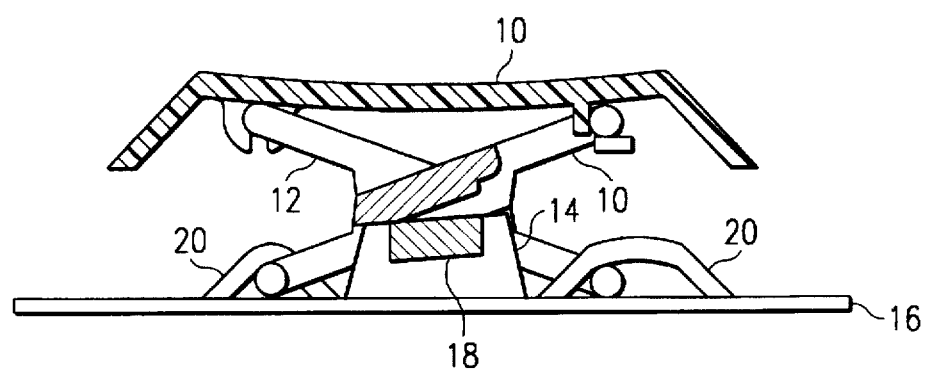
Figure 4A:
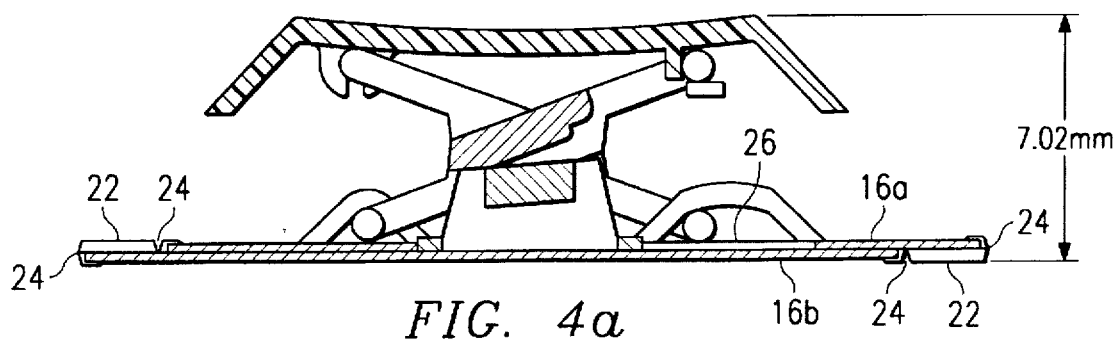
Figure 4B:
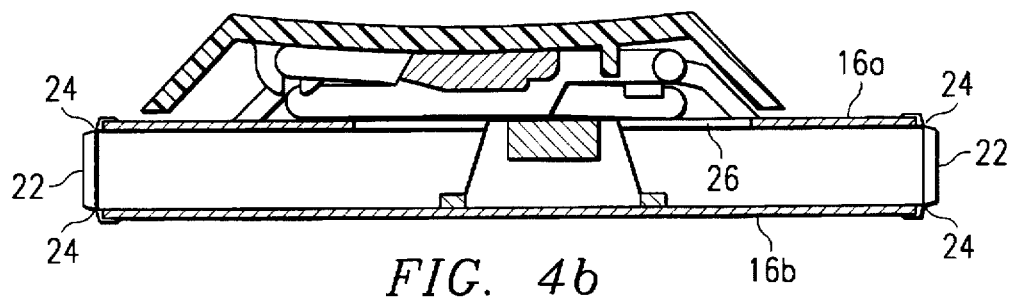
Figure 4C:
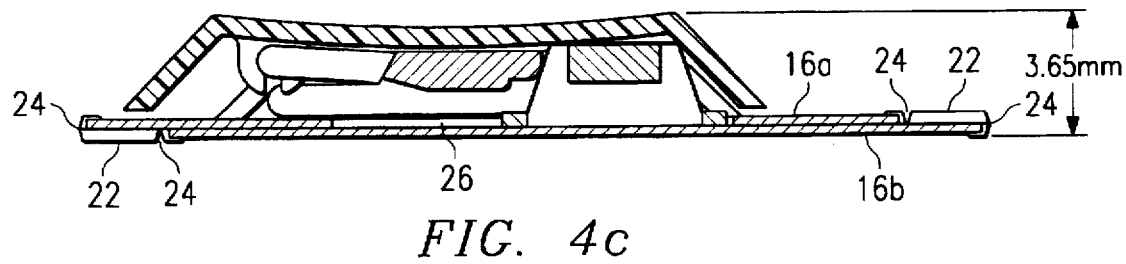
Figure 5A:
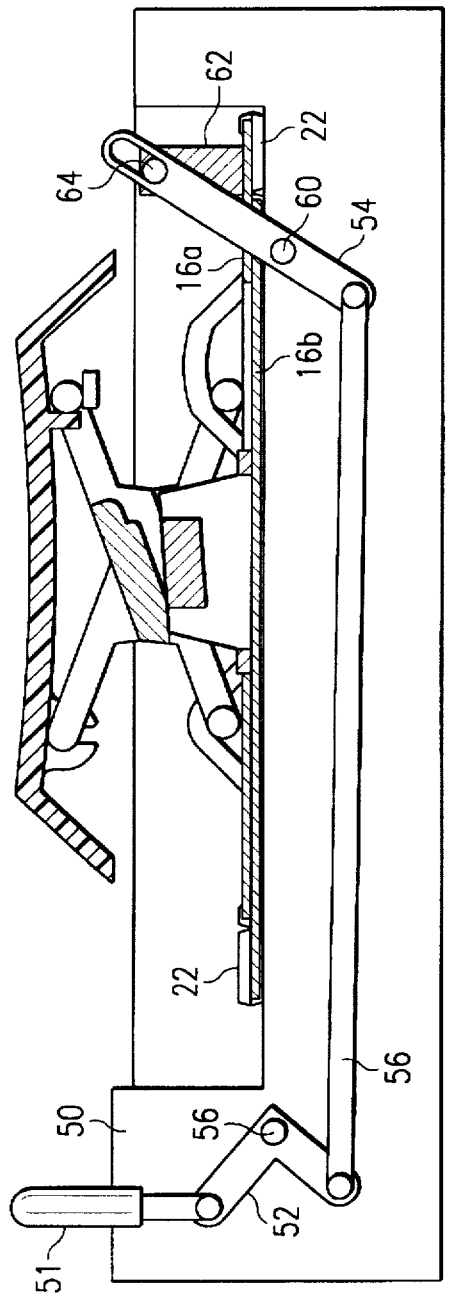
Figure 5B:
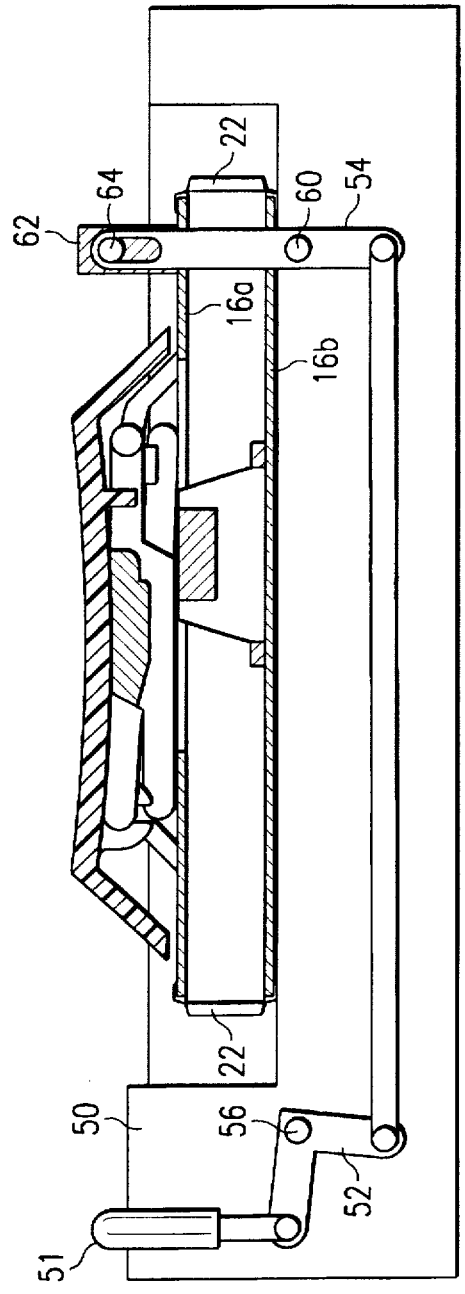
Figure 7A:
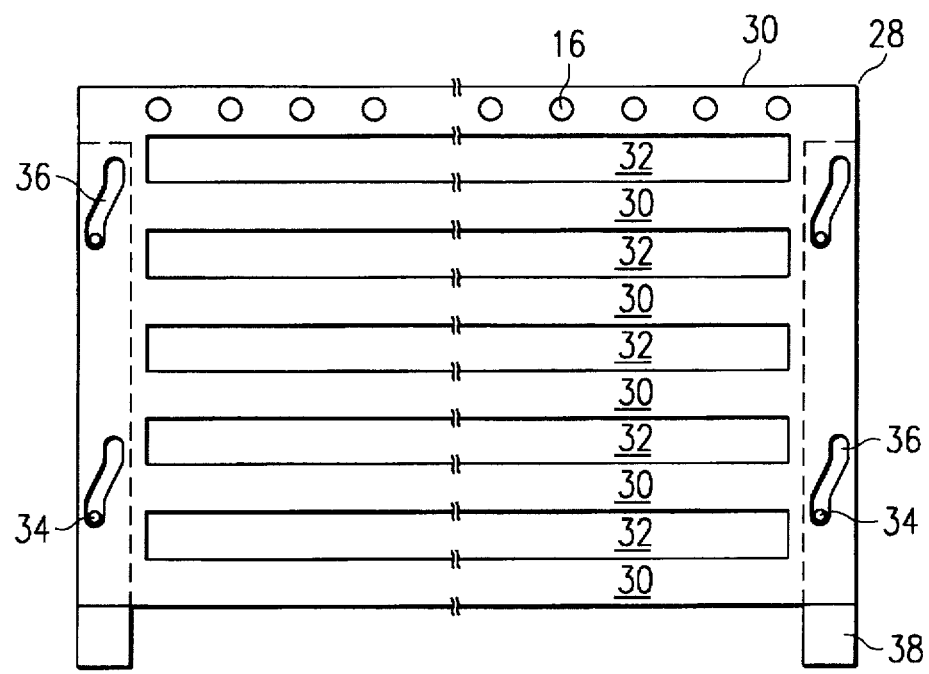
Figure 7B:
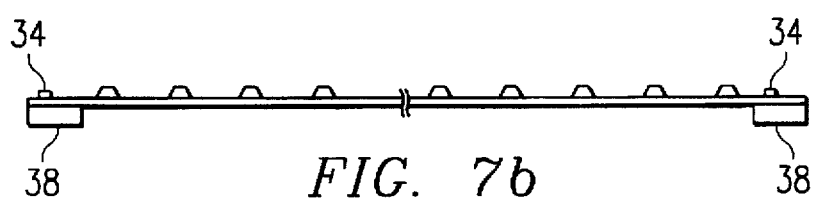
Figure 1:
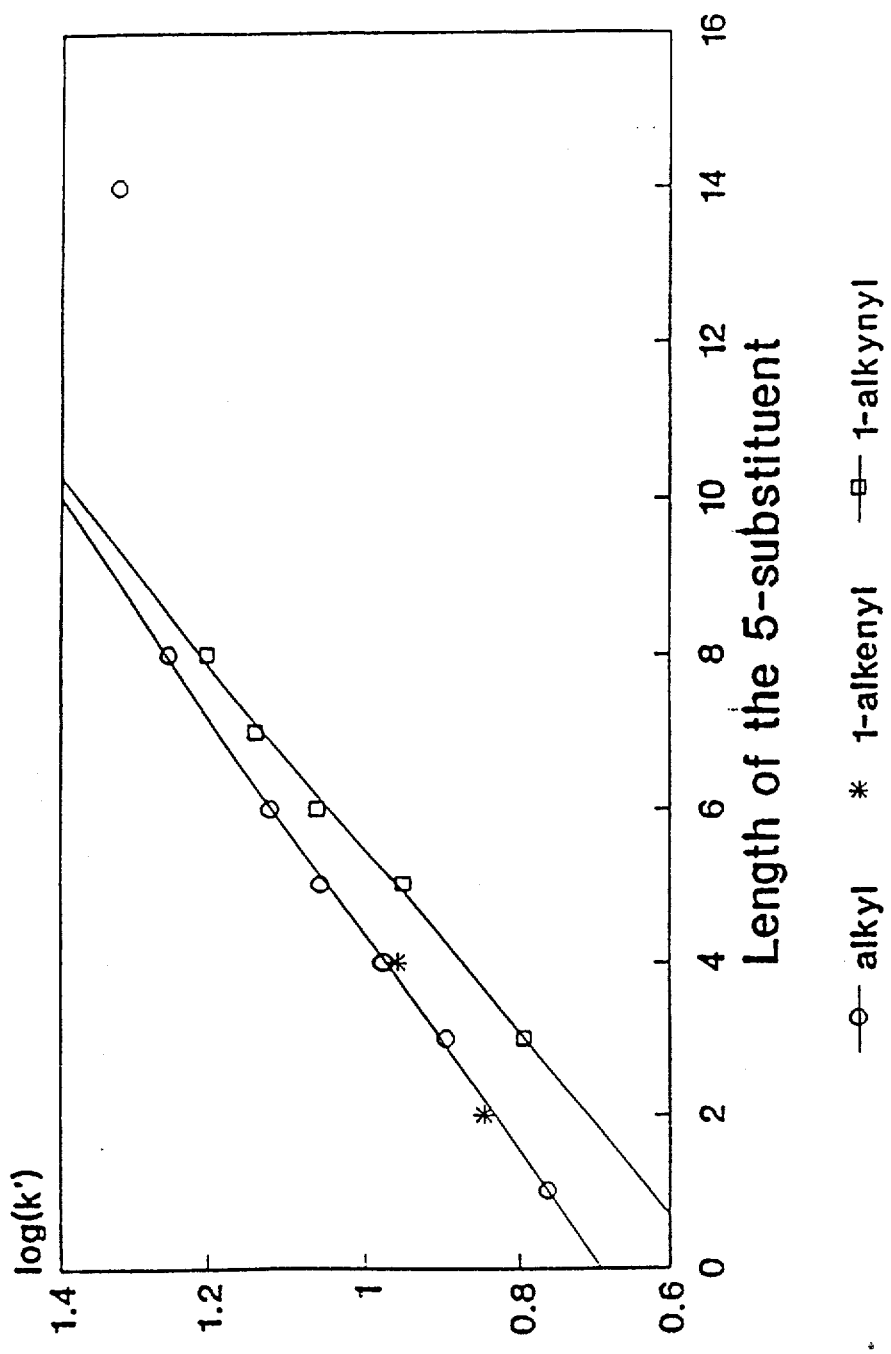
Figure 2:
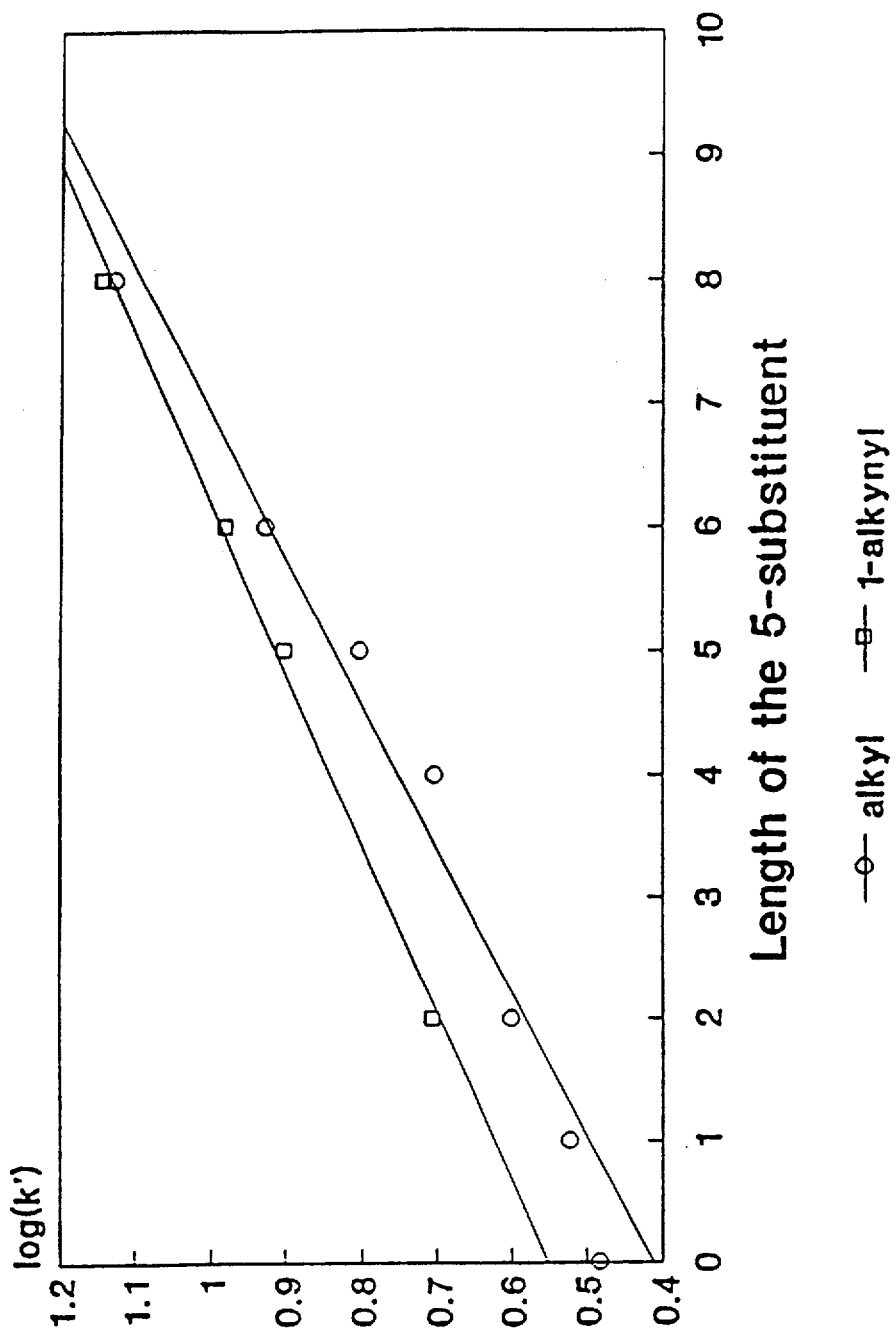

Data presented in Tables 8 and 9 and FIGS. 1 and 2 demonstrate well that there is a good correlation between carbon chain length of the hydrophobic substituent and hydrophobicity of the oligodeoxynucleotide [log(k')] calculated from HPLC retention times. As chain length of the 5-substituent of the pyrimidine bases uracil and cytosine increases, the log(k') value, characteristic of hydrophobicity, increases as well. More precisely, the increase is linear up to the 8-carbon-atom-chain-containing analogs (octyl⁵dU-dA)₁₀, (octynyl⁵dU-dA)₁₀ (FIG. 1) and (octyl⁵dC-dG)₆ and (octynyl⁵dC-dG)₆ (FIG. 2). The (octyl⁵dU-dA)₁₀ is 1.64-times, the (octynyl⁵dU-dA)₁₀ is 1.57-times more hydrophobic than (dT-dA)₁₀. The (octyl⁵dC-dG)₆ is 2.34-times and the (octynyl⁵dC-dG)₆ is 2.38-times more hydrophobic than (dC-dG)₆.

Cellular uptake of the oligodeoxynucleotides as determined by radioisotope-labelled analogs The oligodeoxynucleotides 5'-(dT-dA)₁₀-3' and 5'-(n-alkynyl⁵dU-dA)₁₀-3' were labelled on their 5'-terminal nucleosides thymidine and 5-(1-n-alkynyl)-2'-deoxyuridine with polynucleotide kinase enzyme in the presence of (gamma-³⁵S)ATP as phosphate donor. The 5'-thiophosphate-labelled oligodeoxynucleotides were purified by reversed-phase thin layer chromatography. After removing from the layer by dissolving, the labelled oligodeoxynucleotides were concentrated and then determined by ultraviolet spectrophotometry (HP8452A spectrophotometer interfaced to an AT386 computer) and liquid scintillation (LKB 1217). For the cellular uptake experiments oligodeoxynucleotide solutions with specific activity of 0.5–2.5×10⁶ dpm/microgram were used.

For cellular uptake experiments tumour cell line 205 and MT4 cell lines were used. The cells were transplanted with cell numbers of 5×10⁵ into a 24-well plate in the case of cell line 205 and into a 33 mm diameter Petri dish in the case of the MT4 cells. 48 hours after transplantation 1—1 microgram of labelled oligodeoxynucleotides were added to the solutions containing the cells. Then the solutions were incubated at 37° C. under 5% CO₂ for 3, 6, 10 and 24 hours. The cells were then washed with PBS of 4° C. (Dulbecco buffer, Sigma) to remove labelled oligodeoxynucleotides adsorbed to cell surface. Thereafter the cells were lysed with 1M NaOH solution (0.5 ml). After 24 hours radioactivity was determined from 0.2 ml samples.

Figure 3A:
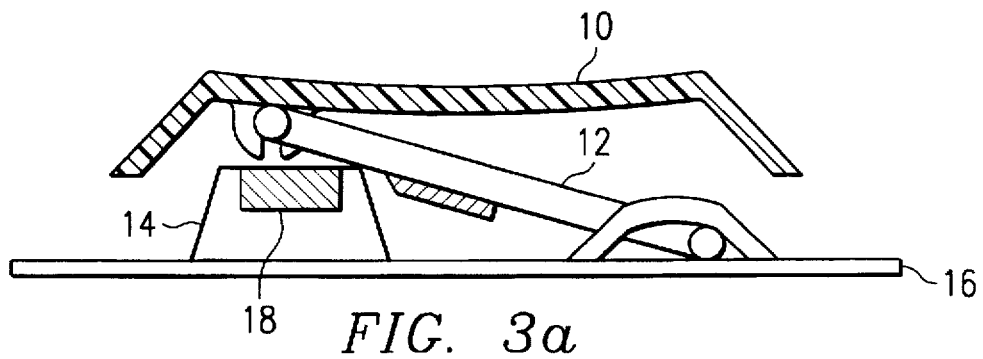
FIG. 3 shows the correlation between hydrophobicity [log(k')] and cellular uptake of oligonucleotides as expressed by radioactivity (dpm/0.2 ml) inside the tumor cells 205. Circles, from left to right, represent (dT-dA)$_{10}$, (propynyl$^5$dU-dA)$_{10}$, (pentynyl$^5$dU-dA)$_{10}$, (hexynyl$^5$dU-dA)$_{10}$, (heptynyl$^5$dU-dA)$_{10}$, (octynyl$^5$dU-dA)$_{10}$.
Figure 3B:
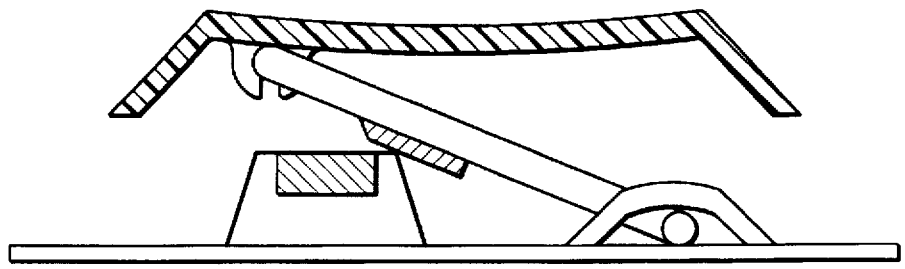
Figure 3C:
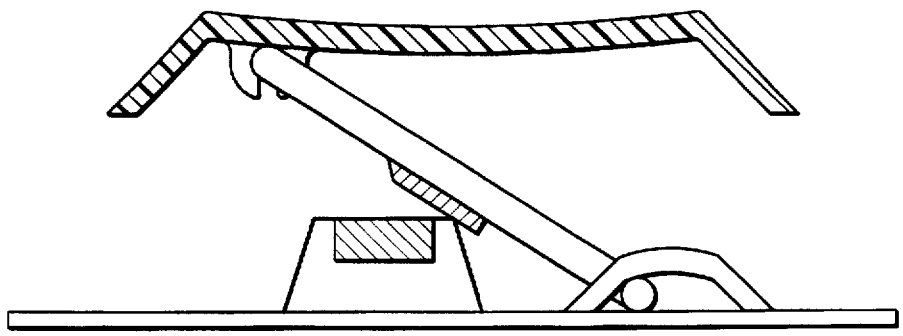
Figure 3:
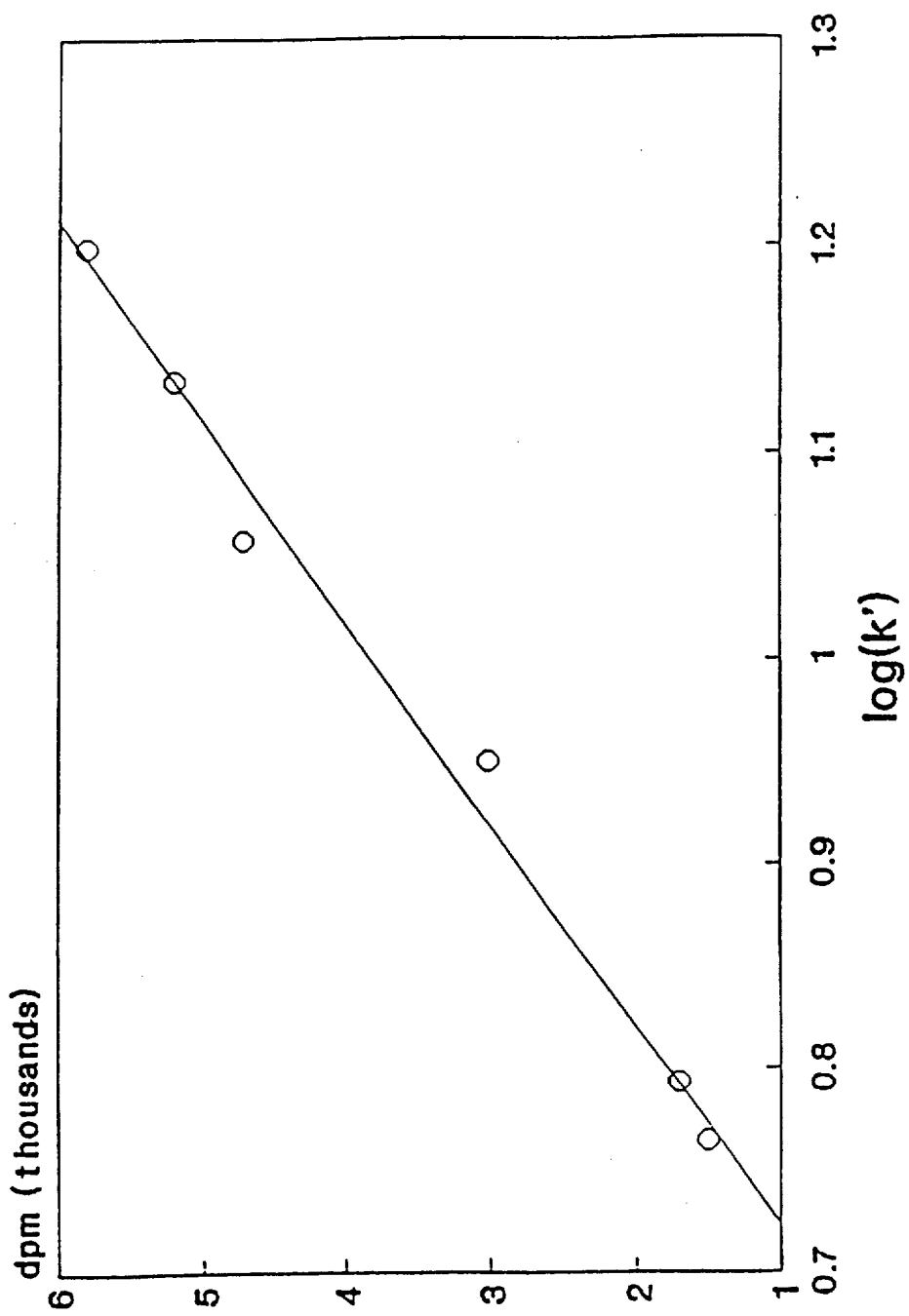

FIG. 3 shows the correlation between hydrophobicity [log(k')] and cellular uptake of the oligodeoxynucleotides as expressed by radioactivity (dpm/0.2 ml) inside the tumour cells 205. Circles from left to right are (dT-dA)₁₀, (propynyl⁵dU-dA)₁₀, (pentynyl⁵dU-dA)₁₀, (hexynyl⁵dU-dA)₁₀, (heptynyl⁵dU-dA)₁₀ and (octynyl⁵dU-dA) ₁₀. FIG. 3 shows that cellular uptake of oligodeoxynucleotides increased upon substitution of position 5 of uracil by 1-alkynyl groups and there is a good correlation between hydrophobicity and cellular uptake of the oligodeoxynucleotide analogs.

Determination of rate of degradation of oligodeoxynucleotides by snake venom phosphodiesterase enzyme The 3'-exonucleases are considered to be the main factor in degrading activity in vivo of the oligodeoxynucleotides (E. Uhlman & A. Peyman: Chem. Rev. 1990, 90, 543–583). The snake venom phosphodiesterase is a 3'-exonuclease. This was used for comparing the rate of hydrolysis of the novel oligodeoxynucleotide analogs with that of the unmodified ones. The kinetic analysis was carried out by a method based on HPLC.

Enzyme reactions were carried out in the physiological buffer 0.1M NaCl, 20 mM sodium phosphate buffer (pH 7.02) and 2 mM MgCl₂ in a final volume of 0.12 ml. Concentration of oligodeoxynucleotide was 1 optical density unit/ml, that of the enzyme was 13.5 microgram/ml. Reaction mixtures were incubated at 37° C. and samples of 0.01 ml were taken at 5, 10, 20 and 30 minutes, respectively, and injected directly on the HPLC column.

HPLC determinations were carried out by a Waters instrument (Waters 510 pumps, Waters 991 diode-array detector, Millipore gradient controller) with an anion-exchange column (Waters Protein PAK, DEAE 5PW, 75×7.5 mm) connected after a guard column (Nucleosil C18, 5×4 mm, BST, Hungary). Gradient A was 0.02M sodium phosphate buffer (pH 3), gradient B was 0.02M sodium phosphate (pH 3) plus 0.5M NaCl, and gradient A 100% to 20% was reached in 20 minutes with a flow rate of 1 ml/min. The rate of hydrolysis was followed by determining the change of peak areas of the cleaved purine nucleotides dAMP and dGMP. With (dT-dA)₁₀ and analogs detection was carried out at 260 nm, with the (dC-dG)₆ and analogs at 280 nm. Absorption data were collected in the range of 250 to 285 nm. Rate of hydrolysis was calculated by the formula $$v = A/(a.e.i)$$

where "v" is rate of hydrolysis, "A" is the peak area of the cleaved purine nucleotide, "a" is amount of the oligodeoxynucleotide in optical density units, "e" is amount of the enzyme phosphodiesterase in micrograms and "i" is time incubation in minutes. The specific absorption area obtained for (dT-dA)₁₀ was 628/(1 unit, 1 microgram, 1 minute) and for (dC-dG)₆ it was 128/(1 unit, 1 microgram 0.1 minute). These values were taken as 100% each and rate values listed in Tables 10 and 11 are expressed relative to them.

TABLE 10

Relative rate of hydrolysis of 5'-(dT-dA)$_{10}$-3' and analogs by snake venom phosphodiesterase enzyme

| Oligodeoxynucleotide | Relative rate of hydrolysis (%) |
|---|---|
| (Propyl$^5$dU-dA)$_{10}$ | 73.6 |
| (Butyl$^5$dU-dA)$_{10}$ | 25.6 |
| (Pentyl$^5$dU-dA)$_{10}$ | 3.2 |
| (Hexyl$^5$dU-dA)$_{10}$ | 0 |
| (Octyl$^5$dU-dA)$_{10}$ | 0 |
| (Tetradecyl$^5$dU-dA)$_{10}$ | 0 |
| (Vinyl$^5$dU-dA)$_{10}$ | 36.6 |
| (Butenyl$^5$dU-dA)$_{10}$ | 17.8 |
| (Pentynyl$^5$dU-dA)$_{10}$ | 0 |
| (Hexynyl$^5$dU-dA)$_{10}$ | 0 |
| (Heptynyl$^5$dU-dA)$_{10}$ | 0 |
| (Octynyl$^5$dU-dA)$_{10}$ | 0 |
| (dT-dA)$_{10}$ | 100 |
| (Propynyl$^5$dU-dA)$_{10}$ | 34.1 |

TABLE 11

Relative rate of hydrolysis of 5'-(dC-dG)$_6$-3' and analogs by snake venom phosphodiesterase enzyme

| Oligodeoxynucleotide | Relative rate of hydrolysis (%) |
|---|---|
| (Butyl$^5$dC-dG)$_6$ | 44.5 |
| (Pentyl$^5$dC-dG)$_6$ | 19.5 |
| (Hexyl$^5$dC-dG)$_6$ | 0 |
| (Octyl$^5$dC-dG)$_6$ | 0 |
| (Etynyl$^5$dC-dG)$_6$ | 13.9 |
| (Pentynyl$^5$dC-dG)$_6$ | 0 |
| (Hexynyl$^5$dC-dG)$_6$ | 0 |
| (Octynyl$^5$dC-dG)$_6$ | 0 |
| (dC-dG)$_6$ | 100 |
| (Hethyl$^5$dC-dG)$_6$ | 87.5 |
| (Ethyl$^5$dC-dG)$_6$ | 78.1 |

Data presented in Tables 10 and 11 prove that substitution of position 5 of the pyrimidines of the oligodeoxynucleotides by 5-n-alkyl, 5-(1-n-alkenyl) and 5-(1-n-alkynyl) groups highly increases their resistance to nucleases. More specifically, rate of hydrolysis by the 3'-exonuclease snake venom phosphodiesterase strongly decreased upon substitution, and (hexyl$^5$dU-dA)$_{10}$, (pentynyl$^5$dU-dA)$_{10}$, (hexyl$^5$dC-dG)$_6$ and (pentynyl$^5$dC-dG)$_6$ and even the longer-chain analogs became resitant to the enzyme during the 30-minute incubation.

For therapeutical application the compounds according to the invention can be converted into pharmaceutical compositions by mixing them with non-toxic, inert and solid or liquid carriers, diluents and/or other additives conventionally used in the pharmaceutical industry, thus producing the usual application forms, e.g. for enteral or parenteral application. Carriers, diluents and excipients that meat the above requirements are for example water, gelatine, lactose, saccharose, starch, pectine, stearic acid, magnesium stearate, talc, various plant oils, furthermore glycols, for example propylene glycol or polyethylene glycol.

Among the pharmaceutical additives preservatives like methyl-(4-hydroxybenzoate), various natural or synthetic emulgeators, dispersing and wetting agents, colouring and flavouring agents, buffers as well as agents for promoting disintegration and dissolving are mentioned.

The conventional pharmaceutical compositions that can be produced by using the above pharmaceutical additives may be solid compositions like tablets, capsules, powders, dragees or granulates, liquid pharmaceutical compositions like syrups, solutions, emulsions or suspensions, furthermore parenteral compositions like injection and infusion solutions as well as compositons for rectal application like suppositories.

The compounds according to the invention exert very low toxicity, they are practically non-toxic. In a MT4 cell culture 100 microgram/ml of (hexynyl$^5$dU-dA)$_{10}$ was found to be non-toxic to cells, viability of the cells did not show any change.

Daily dose of the compositions according to the invention depends on numerous factors, like the type of disease to be treated, the age and condition of the patient to be treated, the mode of application, etc. Practically, 0.5 to 1200 mg/kg body weight is applied daily. Accordingly, it is advantageous to apply tablets, capsules or dragees of 0.01 to 0.2 grams 1 to 3 times daily.

The main advantages of the compounds according to the invention are as follows:

i) They can exert their action through inhibition of expression of the gene responsible for a given disease by forming stable and sequence-specific duplex with a specific region of the mRNA or virus RNA;

ii) They can form duplexes with unaltered or increased stability as compared to unmodified oligodeoxynucleotides;

iii) They possess highly increased nuclease-stability, compared to unmodified oligodeoxynucleotides.

iv) They are much more hydrophobic and thus are much more readily taken up by cells than their unmodified counterparts.

v) They can effectively be used as antisense drugs against various deseases caused by viruses, including HIV, fungi, bacteria or endogenous genes.

The invention is further illustrated by the following non-limiting examples.

EXAMPLE 1

Synthesis of an oligodeoxynucleotide containing 5-(1-n-hexynyl)uracils in place of thymines For the synthesis a Biosearch 8700 DNA Synthesizer was used. The bottle containing a 0.03M solution of 5'-O-(p,p')-dimethoxytrityl-5-(n-1-hexynyl)-2'-deoxyuridine-3'-(2-cyanoethyl-N,N-diisopryl)-phosphoramidate (DMT-2'-deoxy-n-1-hexynyl-CED-phosphoramidate) (Scheme 2) in acetonitrile was placed in positon 13 of the Synthesizer. In positions 9-12 bottles containing similar solutions of CED reagents of natural nucleotides were placed. In position 8 a bottle containing the activating agent tetrazole in 0.47M acetonitrile was placed.

The first nucleotide of an oligodeoxynucleotide to be

Scheme 2

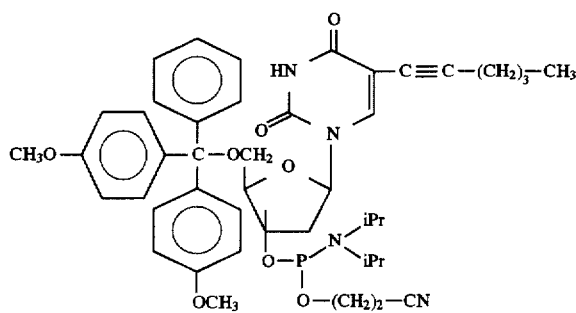

synthesized is bonded via its free 3'-OH group by a covalent linkage to the surface of the controlled pore glass (CPG) matrix through a spacer arm. From this matrix-bonded nucleoside, protected at the 5'-OH group by a dimethoxytrityl group, 1 micromol was filled into a reactor of 1×30 mm which was equipped at both ends with filters and closures. The Synthesizer was programmed according to the sequence of the oligodeoxynucleotide to be synthesized and synthesis was started.

The first step was the removal of the 5'-dimethoxytrityl protecting group from the CPG matrix-bonded nucleoside by a solution of 2.5% dichloroacetic acid in dichloromethane, in 90 seconds. After washing with acetonitrile a condensation reaction followed with the next nucleotide of the sequence to be synthesized: 15 micromol of material from one of the positions of 9–13 and 75 micromol from position 8 was pumped into the reactor and left standing there for 3 minutes. After washing with acetonitrile the unreacted free 5'-OH groups were acetylated with a mixture of acetonitrile-collidine-dimethylaminopyridine-acetic anhydride (73:15:2:10), then the phosphite bond formed during the condensation reaction was oxidized to phosphate with 0.01M iodine solution (acetonitrile-collidine-water=64:6:30). After a washing step the whole cycle began again starting with detritylization until the whole sequence to be synthesized was ready. After condensation of the last nucleotide a final detritylization step followed.

The CPG matrix-bonded oligodeoxynucleotide, containing protecting groups on the heterocyclic bases, was cleaved from the matrix with a 30% $NH_4OH$/water solution in 1 hour. The solution was then heated up to 60°C and held at this temperature for 8 hours to remove all protecting groups from the oligodeoxynucleotide. The solution was then evaporated, extracted with diethyl ether and the water solution was purified by HPLC. The crude oligodeoxynucleotide mixture contained mainly shorter oligodeoxynucleotides as contaminants. The purification of the main component was carried out by reversed-phase HPLC using an ISCO instrument with model 2350 pumps and V4 ultraviolet detector. The pumps were programmed by an IBM-compatible AT286 interfaced to the ISCO with the software ISCO ChemSearch version 2.3. In addition to programming the pumps, the software performed data aquisition and calculations.

The crude oligodeoxynucleotide was first analyzed by using an analytical reverse-phase column (Nucleosil 5, C18, 300 Å, 4.6×250 mm, Phenomenex) with acetonitrile gradient from 5% to 50% in 0.1M potassium phosphate (pH 7) in 45 minutes. Usually 0.05 optical density units (about 1.6 microgram) of the crude mixture were injected onto the column and preparative purification was planned on the basis of the chromatogram obtained. For the preparative scale of separation about 100 units (about 3.3 mg) of crude material was loaded onto a 10×250 mm semi-preparative column (Nucleosil 5, C18, 300 Å, Phenomenex) and the same acetonitrile gradient was used for separation.

All chromatographic peaks were collected, in addition to the main peak, in order to be able to calculate yield. The amount of material collected was determined by ultraviolet spectrophotometry. Acetonitrile was then removed from the solution corresponding to the main chromatographic peak by vacuum evaporation. The remaining water solution was further concentrated by centrifugal evaporation (Vacu-Spin, Virtis, USA) to 5–10 ml. This solution was then desalted by dialysis in a low-molecular-weight cut-off (6000 Daltons) dialysis bag (Spectrum Med. Ind., Inc., L.A., USA). The dialysis was carried out against ion-free water and removal of salt from the bag was followed by measuring increase of conductivity of the water outside. The desalted solution of the purified oligodeoxynucleotide was then freeze-dried and held at –25°C.

The yield of the condensation reaction in the Synthesizer was about 97%. In this way, a 20 nucleotide-long oligodeoxynucleotide was obtained in about 55% final yield which corresponded to about 100 optical density units measured at 260 nm. After reverse-phase HPLC purification the total final yield was generally 50 units (about 1.65 mg) of the pure 20-mer oligodeoxynucleotide.

EXAMPLE 2

Synthesis of an oligodeoxynucleotide containing 5-(1-n-hexynyl)cytosines in place of cytosines The preparation of the oligodeoxynucleotide was carried out as described in Example 1 with the difference that the bottle placed in position 13 of the DNA Synthesizer contained 10 ml of 0.04M 4-benzoyl-5-(n-1-hexynyl)-2'-deoxycytidine-CED (Scheme 3) solution. The condensation step lasted a minute.

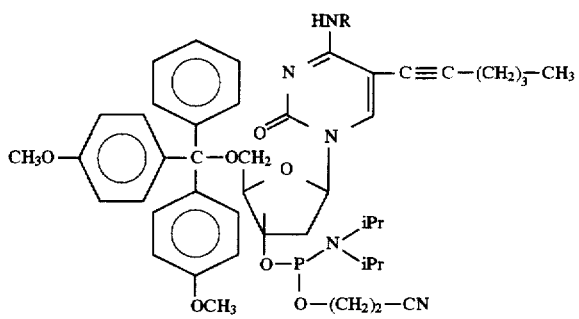

Scheme 3

EXAMPLE 3

Synthesis of an oligodeoxynucleotide containing 5-(1-n-hexynyl)uracils in place of thymines and 5-(1-n-hexynyl) cytosines in place of cytosines The preparation of the oligodeoxynucleotide was carried out as described in Example 1 with the difference that the bottle placed in position 12 of the DNA Synthesizer contained 10 ml of 0.04M 4-benzoyl-5-(n-1-hexynyl) -2'-deoxycytidine-CED. The condensation step lasted 4 minutes.

EXAMPLE 4

Synthesis of a phosphorothioate oligodeoxynucleotide containing 5-(1-n-hexynyl)uracils in place of thymines The preparation of the oligodeoxynucleotide where the phosphodiester linkages were replaced by phosphorothioate ones as it can be seen for the 5-(1-n-hexynyl)-2'-deoxyuridine unit on Scheme 4

Scheme 4

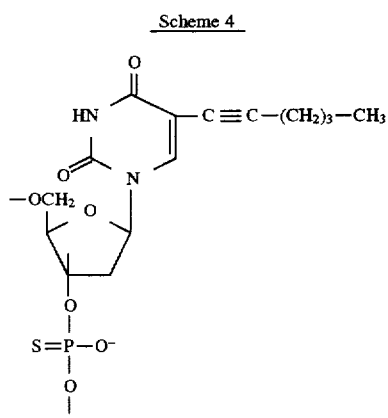

was carried out as described in Example 1 with the following modifications:

i) Oxidation step: after each condensation step the oligodeoxynucleotide solution was treated with a solution of 0.5M tetraethylthiuram-disulphide in acetonitrile for 20 minutes, followed by the usual washing step by acetonitrile.

ii) Acetylation of the unreacted 5'-OH groups: after the above step i) the oligodeoxynucleotide solution was treated with a mixture of acetonitrile-collidine-acetic anhydride-(N-methyl-imidazole) (65:15:10:13) for 1 minute, then washed with acetonitrile.

iii) The main HPLC peak of the preparative reverse-phase chromatographic purification was repeatedly purified by HPLC.

What is claimed is:

1. A 12 to 30 nucleotide-unit long oligodeoxynucleotide comprising at least one 5-substituted uracil or cytosine, where the 5-substituent is a $C_{3-6}$ n-alkyl group, a vinyl group, a butenyl group, an ethynyl group or a $C_{4-12}$ n-1-alkynyl group, with the proviso that the uracil moiety may not be substituted with an n-alkyl group or a $C_{8-12}$ n-1-alkynyl group.

2. An oligodeoxynucleotide as claimed in claim 1, in which one or more of the phosphodiester moieties are replaced by phosphorothioate or phosphorodithioate moieties.

3. An oligodeoxynucleotide as claimed in claim 1, in which one or more of the phosphodiester moieties are replaced by phosphorothioate moieties of R- or S-configuration.

* * * * *

UNITED STATES PATENT AND TRADEMARK OFFICE
CERTIFICATE OF CORRECTION

PATENT NO.: 5,767,264

DATED: June 16, 1998

INVENTOR(S): OTVOS et al.

It is certified that error appears in the above-identified patent and that said Letters Patent is hereby corrected as shown below:

On the cover page, insert the following correct priority information:

-- [30]  Foreign Application Priority Data
  Jan. 22, 1993     [HU] ................ 93 000174--.

Signed and Sealed this

Sixth Day of October, 1998

*Attest:*

BRUCE LEHMAN

*Attesting Officer*     Commissioner of Patents and Trademarks

UNITED STATES PATENT AND TRADEMARK OFFICE
CERTIFICATE OF CORRECTION

PATENT NO.: 5,767,264　　　　　　　　　　　Page 1 of 4

DATED: 　　　June 16, 1998

INVENTOR(S): OTVOS et al.

It is certified that error appears in the above-identified patent and that said Letters Patent is hereby corrected as shown below:

On cover page, "6 Drawing Sheets" should read --3 Drawing sheets--

On the cover page, item [73], "MTA Zozponti Kemiai Kutato" should read
--MTA Központi Kémiai Kutató Intézet--.

The drawings sheets, consisting of Figs. 1 - 7b, should be deleted to be replaced with the drawing sheets, consisting of Figs. 1 - 3, as shown on the attached pages.

Signed and Sealed this

Twenty-ninth Day of December, 1998

Attest:

BRUCE LEHMAN

Attesting Officer　　　　Commissioner of Patents and Trademarks